United States Patent
Ferrick et al.

(10) Patent No.: US 11,940,442 B2
(45) Date of Patent: Mar. 26, 2024

(54) METHOD AND SYSTEM FOR DETERMINING INTEGRATED METABOLIC BASELINE AND POTENTIAL OF LIVING CELLS

(71) Applicant: AGILENT TECHNOLOGIES, INC., Santa Clara, CA (US)

(72) Inventors: David A. Ferrick, El Macero, CA (US); Brian Dranka, Acton, MA (US)

(73) Assignee: Agilent Technologies, Inc., Santa Clara, CA (US)

(*) Notice: Subject to any disclaimer, the term of this patent is extended or adjusted under 35 U.S.C. 154(b) by 348 days.

(21) Appl. No.: 16/917,352

(22) Filed: Jun. 30, 2020

(65) Prior Publication Data
US 2020/0333327 A1    Oct. 22, 2020

Related U.S. Application Data

(63) Continuation of application No. 15/082,658, filed on Mar. 28, 2016, now abandoned.

(60) Provisional application No. 62/139,432, filed on Mar. 27, 2015.

(51) Int. Cl.
G01N 33/50    (2006.01)

(52) U.S. Cl.
CPC ..... G01N 33/5091 (2013.01); G01N 33/5005 (2013.01)

(58) Field of Classification Search
None
See application file for complete search history.

(56) References Cited

U.S. PATENT DOCUMENTS

| | | | |
|---|---|---|---|
| 7,638,321 B2 | 12/2009 | Teich et al. | |
| 2007/0087401 A1 | 4/2007 | Neilson et al. | |
| 2012/0294956 A1 | 11/2012 | Qian et al. | |

FOREIGN PATENT DOCUMENTS

| | | |
|---|---|---|
| CN | 104704361 A | 6/2015 |
| JP | 2018509170 A | 4/2018 |

(Continued)

OTHER PUBLICATIONS

Determining the Energy Phenotype of Cells, XF Cell Energy Phenotype Test Data Flyer, Apr. 17, 2015.

(Continued)

*Primary Examiner* — David W Berke-Schlessel

(57) ABSTRACT

The current technology is related to methods for rapidly determining the metabolic baseline and potential of living cells. Embodiments relate to measuring the activity of each of the two major energy-generating pathways within the cell: mitochondrial respiration and glycolysis, first under baseline conditions, and again after applying a stress to the cells to demand increased energy supply. In some embodiments the stress may be applied by exposing the cells to a combination of two chemical compounds: a mitochondrial uncoupler and an ATP synthase inhibitor. In one embodiment, the metabolic energy generating activity of the mitochondrial respiration pathway is determined by measuring the rate of oxygen consumption by the living cells, and the metabolic energy generating activity of the glycolysis pathway is determined from a measurement of extracellular acidification caused by secretion of protons from the cell. Other embodiments are related to an apparatus for determining a metabolic potential of a cell sample in a well of a multiwell plate.

15 Claims, 10 Drawing Sheets

(56) References Cited

FOREIGN PATENT DOCUMENTS

| WO | 2012016018 A1 | 2/2012 |
|----|---------------|--------|
| WO | 2016160702 A1 | 10/2016 |

OTHER PUBLICATIONS

Seahorse XF Glycolysis Stress Test Kit, User Guide, Apr. 17, 2015.
Seahorse XFp Cell Energy Phenotype Test Kit, User Guide, Apr. 17, 2015.
Seahorse XFp Cell Energy Phenotype Test Kit Flyer, Seahorse Bioscience, Apr. 17, 2015.
Bradford, et al., "Importance of The Bioenergetic Reserve Capacity In Response To Cardiomyocyte Stress Induced By 4-Hydroxynonenaln", Biochemical Journal, vol. 424, No. 1, Nov. 15, 2009, 99-107.
Bugge, et al., "Measuring Respiratory Activity of Adipocytes and Adipose Tissues in Real Time", Methods in Enzymology, vol. 538, 2014, 233-247.
Choi, et al., "Bioernergetic analysis of isolated cerebrocortical nerve terminals on a microgram scale: spare respiratory capacity and stochastic mitochondrial failure", J. Neurochem, vol. 109, 2009, 1179-1191.
Dranka, et al., "Assessing bioenergetic function in response to oxidative stress by metabolic profiling", Free Radical Biology & Medicine, vol. 51, 2011, 1621-1635.
Extended European Search Report dated Jul. 13, 2018, Application No. 16773926.7, 8 pages.
Extended European Search Report dated Jun. 12, 2020, Application No. 20150661.5, 10 pages.
Ferrick, et al., "Advances In Measuring Cellular Bioenergetics Using Extracellular Flux", Drug Discovery Today, vol. 13, No. 5/6, Mar. 2008, 268-274.
Hill, et al., "Importance of the bioenergetic reserve capacity in response to cardiomyocyte stress induced by 4 hydroxynonenal", Biochem J., vol. 424, 2009, 99-107.
Ibrahim-Hashim, et al., "Free Base Lysine Increases Survival and Reduces Metastasis in Prostate Cancer Model", J Cancer Sci Ther., Suppl 1 (4), Nov. 19, 2011, 1-12.
Nicholls, et al., "Bioenergetic profile experiment using C2C12 myoblast cells", JOVE (Journal of Visualized Experiments), vol. 46, Article No. e2511, 2010, 1-6.
International Search Report dated Jul. 25, 2016, International Application No. PCT/US2016/024514, 5 pages.
Pelletier, et al., "Extracellular Flux Analysis to Monitor Glycolytic Rates and Mitochondrial Oxygen Consumption", Methods in Enzymology, vol. 542, Jan. 1, 2014, 125-149.
Pike, et al., "Inhibition of fatty acid oxidation by etomoxir impairs NADPH production and increases reactive oxygen species resulting in ATP depletion and cell death in human", Biochim., Biophys., Acta, 2010.
Reily, et al., "Mitochondrially Targeted Compounds and their Impact on Cellular Bioenergetics", Redox Biology, vol. 1, No. 1, Dec. 31, 2013, 86-93.
Winer, et al., "Rapid Analysis of Glycolytic and Oxidative Substrate Flux of Cancer Cells in a Microplate", Plos One, vol. 9, No. 10, Jan. 31, 2014, 1-14.
EPO, "Extended European Search Report dated May 3, 2022," Application No. 22150034.1, 10 pages.
Hill, Bradford G. et al., "Importance of the Bioenergetic Reserve Capacity in Response to Cardiomyocyte Stress Induced by 4-Hydroxynonenal," Biochemical Journal, vol. 1741, No. 1, Nov. 15, 2009, 19 pages.
Agliano, et al., "Evaluating the glycolytic potential of mouse costimulated effector CD8+ T cells ex vivo," STAR Protocols 3, 101441, Jun. 17, 2022 © 2022 The Author(s); open access article under the CC BY-NC-ND license (http://creativecommons.org/licenses/by-nc-nd/4.0/).
Mercier-Letondal, et al., "Validation of a method evaluating T cell metabolic potential in compliance with ICH Q2 (R1)", J Transl Med (2021) 19:21, https://doi.org/10.1186/s12967-020-02672-7.

Exemplary Data

Screen shot of an exemplary user interface:

METHOD AND SYSTEM FOR DETERMINING INTEGRATED METABOLIC BASELINE AND POTENTIAL OF LIVING CELLS

RELATED APPLICATIONS

This application claims the benefit of U.S. Provisional Application No. 62/139,432, filed on Mar. 27, 2015, the entire disclosure of which is hereby incorporated by reference.

BACKGROUND

Seahorse Bioscience has developed two independent tests of metabolic baseline and potential for each of the two primary energy-generating pathways of cells. Each test requires the addition of three chemical compounds and measurement of activity of one metabolic pathway. Exemplary publications regarding the mitochondrial function test include S. W. Choi, et al., *J. Neurochem.* (2009) 109, 1179-1191; L. S. Pike et al., *Biochim. Biophys. Acta* (2010), doi:10.1016/j.bbabio.2010.10.022; B. B. Hill, *Biochem. J.* (2009) 424, 99-107; D. G. Nichols, et al., JoVE. (2010) 46. wwwjove.com/details.php?id-2511, doi:10.3791/2511; B. P. Dranka et al., *Free Radical Biology & Medicine* 51 (2011) 1621-1635. Exemplary publications regarding the glycolysis function test include Pike et al., and A. Ibrahim-Hashim, et al, *J. Cancer Sci Ther*. (Nov. 19, 2011), Suppl 1(4). The combined measurement of both pathways is disclosed in D. A. Ferrick, et al., Drug Discovery Today (March 2008) 13, 5/6.

SUMMARY OF THE INVENTION

Embodiments of the invention include the combination of certain chemical compounds to measure both metabolic pathway baselines and potentials simultaneously using a single exposure of the combined compounds to the living cells. Surprisingly, the measured result from this test provides robust measurements of the two pathways simultaneously.

Embodiments of the invention enable the stimulation of both major metabolic/energetic pathways acutely with a single injection, as well as the determination of the metabolic potential of these major pathways, i.e., mitochondrial respiration and glycolysis, based on that single injection.

Mitochondria and glycolysis produce the majority of energy for the cell in terms of ATP and is indispensible for biosynthetic reactions that create biomass and cellular constituents.

Prior approaches have been limited to stimulating and analyzing the two major energetic pathways individually. Prior approaches are not able to identify and deliver compound(s) capable of stimulating both major energetic pathways simultaneously. Moreover, prior approaches are not able to measure the simultaneous response of the two major energetic pathways to stress.

For at least four reasons, identification and delivery of compounds capable of stimulating both pathways simultaneously is not obvious to one of skill in the art. First of all, until Seahorse Bioscience commercialized its extracellular flux ("XF") instruments, no technology was capable of measuring both pathways in living cells, so very few even considered the question. Secondly, the vast majority of those trained in the art are either experts on mitochondria or experts in glycolysis. Metabolism is a huge collection of many "subsystems" of which mitochondria and glycolysis are but two. In the majority of diseases and disciplines where metabolism is studied, those trained in the art only focus on the subsystems most relevant to their research and therefore would not know how to perform an experiment relevant to both pathways and as well interpret it.

Thirdly, the two compounds delivered in a single injection in embodiments of the invention, uncoupler and ATP synthase inhibitor (oligomycin), were developed for studying mitochondria and not glycolysis. Seahorse Bioscience is the first company to use the ATP synthase inhibitor to understand glycolytic function, although many researchers demonstrated its use in understanding mitochondrial function. For example, Seahorse was the first to employ oligomycin as a stressor for the glycolytic system in its glycolysis stress test.

Finally, those of skill in the art assume that glycolysis and oxidative phosphorylation work to compensate for each other. Accordingly, previous approaches are generally based on the premise of stimulating one pathway and decreasing the other. Embodiments of the invention include an approach that is fundamentally different, as both pathways are expected to be stimulated simultaneously.

Seahorse Bioscience has demonstrated technology that allows one to measure oxygen consumption rate ("OCR") and extracellular acidification rate ("ECAR") simultaneously. See Ferrick et al. No one, however, has shown injection of both an uncoupler and ATP synthase inhibitor, at the same time, to stress both energetic pathways simultaneously to provide a single indication of metabolic potential and hence phenotype. One may independently determine the stressed responses using two separate approaches and two separate samples, and then combine the data mathematically to determine a total. In contrast, methods in accordance with embodiments of the invention described herein employ a single sample and a single injection, whereby the user can determine a single metabolic baseline and potential of the cell that is representative of both mitochondrial respiration and glycolysis.

Methods in accordance with the embodiments of the invention described herein have a number of significant advantages over prior art methods of determining the metabolic capacity of cells. For example, because dosing of uncoupler and ATP synthase inhibitor is done via a single injection, data may be collected much more rapidly, allowing metabolic capacity to be measured on a high-throughput scale. For example, prior art methods required a 20 minute interval between dosing of the ATP synthase inhibitor and dosing of the uncoupler; which is eliminated in the methods described herein. Instead, methods in accordance with certain embodiments of the invention described herein require less than the 20 minute interval between dosing of the ATP synthase inhibitor and dosing of the uncoupler of the prior art methods. For example, certain methods in accordance with certain embodiments of the invention described herein demonstrate that the interval between dosing of the ATP synthase inhibitor and dosing of the uncoupler is less than 20 minutes, less than 15 minutes, less than 10 minutes, less than 5 minutes, less than 2 minutes or less than 1 minute. Other methods in accordance with certain embodiments of the invention described herein demonstrate that the ATP synthase inhibitor and the uncoupler can be dosed simultaneously or essentially at the same time (e.g., immediately sequentially).

Similarly, the number of cell samples used in a given experiment can be reduced by half as compared to prior art methods which measure OCR and ECAR in parallel in separate samples. This is a key advantage for researchers dealing with rare or difficult to cultivate cell types, particularly primary cell cultures. Combining the uncoupler and ATP synthase inhibitor into a single injection frees elements of the dispensing system, allowing for more complicated experiments. Finally, because the ratio of uncoupler and ATP synthase inhibitor is fixed for each replicate, an important source of variation is removed from the data obtained by the methods disclosed herein, as compared with prior art methods.

In an aspect, some embodiments of the invention include a method of determining a metabolic potential of a cell sample. An initial oxygen consumption rate and an initial extracellular acidification rate of the cell sample are simultaneously measured. Thereafter, a mitochondrial uncoupling agent and an ATP synthase inhibitor are simultaneously administered to the cell sample. Thereafter, a subsequent oxygen consumption rate and a subsequent extracellular acidification rate of the cell sample are simultaneously measured. A metabolic potential of the cell sample is determined.

One or more of the following features may be included. At least one of the mitochondrial uncoupling agent may include carbonyl cyanide p-trifluoromethoxyphenylhydrazone ("FCCP"), carbonyl cyanide-m-chlorophenylhydrazone ("CCCP") or 2,4-dinitrophenol (DNP) or BAM15, or the ATP synthase inhibitor may include oligomycin or 7-Chloro-5-(4-hydroxyphenyl)-1-methyl-3-(napthalen-2-yl-metyl)-4,5-dihydro-1H-benzo[b][1,4]diazepin-2(3H)-one (Bz-423).

The mitochondrial uncoupling agent may include carbonyl cyanide p-trifluoromethoxyphenylhydrazone ("FCCP") and the ATP synthase inhibitor may include oligomycin.

The cell sample may include a plurality of cells disposed in a media. Measuring the initial oxygen consumption rate and/or measuring the initial extracellular acidification rate of the cell sample include sensing a cell constituent disposed in the media.

A concentration of the administered mitochondrial uncoupling agent in the media may be in a range of about 0.1 µM to about 2.0 µM, e.g., about 0.5 µM. A concentration of the administered ATP synthase inhibitor in the media is about 0.1 µM to about 2 µM, e.g., about 1.0 µM. The mitochondrial uncoupling agent and the ATP synthase inhibitor may be mixed prior to administering to the cell sample.

The cell sample may be disposed in a well of a multi-well plate prior to the simultaneous measurement of the initial oxygen consumption rate and the initial extracellular acidification rate of the cell sample. The mitochondrial uncoupling agent and the ATP synthase inhibitor may be administered by simultaneously introducing the agent and the inhibitor simultaneously into the well from at least one port.

Determining the metabolic potential of the cell sample may include (i) providing the initial oxygen consumption rate, the initial extracellular acidification rate, the subsequent oxygen consumption rate, and the subsequent extracellular acidification rate to a software program, and (ii) using the software program to calculate the metabolic potential.

In another aspect, embodiments of the invention include an apparatus for determining a metabolic potential of a cell sample in a well of a multiwell plate. The apparatus includes (i) a stage adapted to support a multiwell plate; (ii) a sensor adapted to sense a cell constituent associated with the cell sample in a well of the multiwell plate; and (iii) a dispensing system adapted to introduce fluids into the well. The stage, sensor, and dispensing system cooperate to simultaneously measure an initial oxygen consumption rate and an initial extracellular acidification rate of the cell sample using the sensor. Thereafter, the dispensing system is used to simultaneously administer to the cell sample a mitochondrial uncoupling agent and an ATP synthase inhibitor. Thereafter, simultaneously a subsequent oxygen consumption rate and a subsequent extracellular acidification rate of the cell sample are measured using the sensor. The metabolic potential of the cell sample is determined.

One or more of the following features may be included. The dispensing system may include at least one port disposed above the well. The sensor may include an optical sensor. The sensor may be adapted to sense a fluorophore. The apparatus may include a computer module and software adapted to calculate the metabolic potential based on information communicated to the computer module by the sensor.

DETAILED DESCRIPTION

Figure 1:
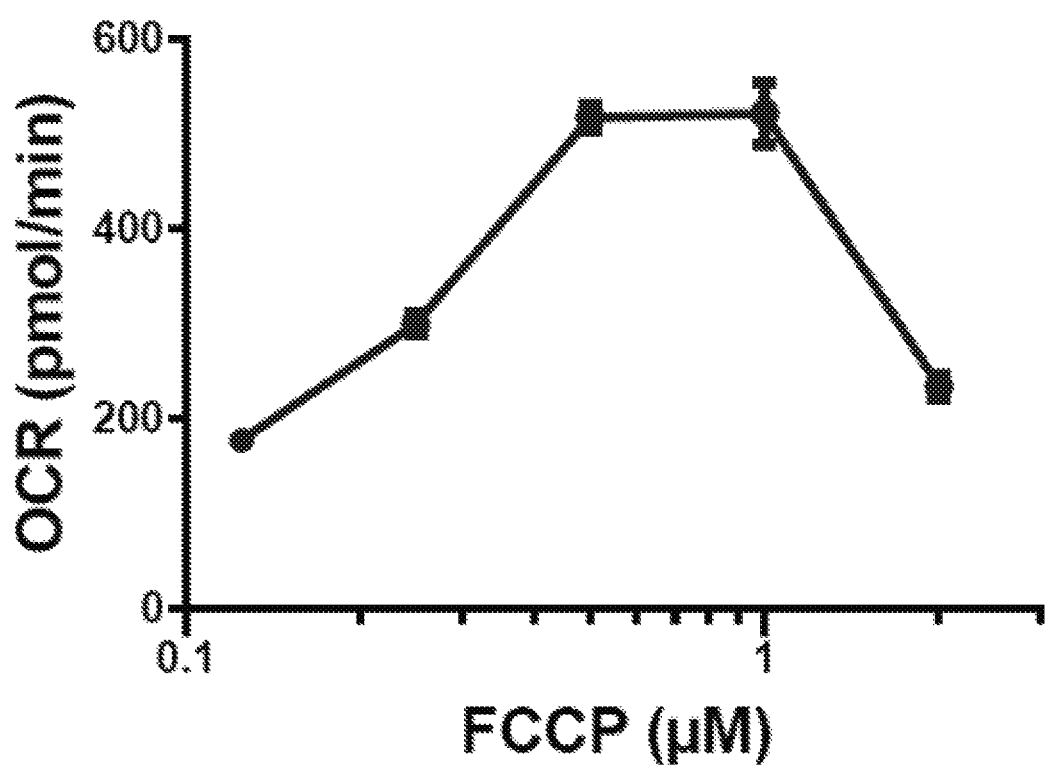
FIG. 1 is a graph showing the results from an FCCP titration in the presence of oligomycin in RAW 264.7 macrophage cells.

The cell energy phenotype test is a method for rapidly determining the metabolic baseline and potential of living cells. This is accomplished by measuring the activity of each of the two major energy-generating pathways within the cell: mitochondrial respiration and glycolysis, first under baseline conditions, and again after applying a stress to the cells to demand increased energy supply.

The stress may be applied by exposing the cells to a combination of two chemical compounds: a mitochondrial uncoupler and an ATP synthase inhibitor. These chemical compounds increase the apparent energy demands on the two metabolic pathways, causing the activity within each pathway to increase to as much as a maximum capacity.

The difference in measured energy generating activity between the stressed and baseline condition defines the metabolic potential. The combination of the metabolic baseline and metabolic potential constitutes the energy phenotype of the cell.

In one embodiment, the metabolic energy generating activity of the mitochondrial respiration pathway is determined by measuring the rate of oxygen consumption by the living cells, and the metabolic energy generating activity of the glycolysis pathway is determined from a measurement of extracellular acidification caused by secretion of protons from the cell.

Experimental Approach

In accordance with embodiments of the invention, the prototypic uncoupler, carbonyl cyanide p-trifluoromethoxyphenylhydrazone ("FCCP"), stresses the aerobic system by dissipating the proton gradient across the inner mitochondrial membrane. This forces the cell to increase mitochondrial activity up to its maximum. Oligomycin blocks the ATPase of complex V, thus preventing the hydrolysis of adenosine triphosphate ("ATP"), that would supply electrons through this complex in the reverse direction which would counteract the effects of FCCP. Oligomycin also "stresses" the glycolytic system to produce more ATP to counteract the loss of ATP caused by its inhibition of the mitochondrial ATPase.

Materials Required

1. An analytical tool suitable for performing analysis in accordance with embodiments of the invention may be, e.g., any one of the following instruments:
   a. Seahorse Bioscience XFp Extracellular Flux Analyzer
   b. Seahorse Bioscience XFe24 Extracellular Flux Analyzer
   c. Seahorse Bioscience XFe96 Extracellular Flux Analyzer
   d. Seahorse Bioscience XF24 Extracellular Flux Analyzer
   e. Seahorse Bioscience XF24-3 Extracellular Flux Analyzer
   f. Seahorse Bioscience XF96 Extracellular Flux Analyzer Each of these apparatus enable one to determine a metabolic potential of a cell sample in a well of a multiwell plate. The apparatus includes (i) a stage adapted to support a multiwell plate; (ii) a sensor adapted to sense a cell constituent associated with the cell sample in a well of the multiwell plate; and (iii) a dispensing system adapted to introduce fluids into the well. Components of the apparatus are described in, e.g., U.S. Pat. Nos. 7,276,351 and 8,658,349, which are both incorporated, in their entireties, by reference herein.

As discussed below, the stage, sensor, and dispensing system cooperate to simultaneously measure an initial oxygen consumption rate and an initial extracellular acidification rate of the cell sample using the sensor. Thereafter, the dispensing system is used to simultaneously administer to the cell sample a mitochondrial uncoupling agent and an ATP synthase inhibitor. Thereafter, a subsequent oxygen consumption rate and a subsequent extracellular acidification rate of the cell sample are simultaneously measured using the sensor. The metabolic potential of the cell sample is determined.

2. Cell culture media. Typically Dulbecco's Modified Eagle's medium ("DMEM"), available from Invitrogen, supplemented with 10 mM glucose, 2 mM glutamine, and 1 mM pyruvate.
3. Assay media (typically DMEM supplemented with glucose, glutamine, and pyruvate, but omitting sodium bicarbonate; available from Seahorse Bioscience as XF Base Medium and supplemented with 10 mM glucose, 2 mM glutamine, and 1 mM pyruvate.
4. Assay cartridge appropriate for the instrument being used, e.g., XFe96 FluxPak.
5. Cells in culture (typically mammalian although not limited to this.) The number of cells required varies based on the instrument used and the type of cell. Typically the number is between 10,000 and 1,000,000 per well. In a prototypical example utilizing RAW 264.7 macrophage cells, 80,000 cells may be seeded per well of an XFp miniplate.
6. Reagents (either a or b)
   a. Oligomycin and FCCP (each available from Seahorse Bioscience)
   b. For the XFp instrument, oligomycin and FCCP are offered as a kit, i.e., the XFp Cell Energy Phenotype Test Kit Generally, reagents preferably include a combination of a mitochondrial uncoupling agent and an ATP synthase inhibitor. Suitable mitochondrial uncoupling agent include, e.g., carbonyl cyanide p-trifluoromethoxyphenylhydrazone ("FCCP"), carbonyl cyanide-m-chlorophenylhydrazone ("CCCP") or 2,4-dinitrophenol ("DNP") or BAM15. Suitable ATP synthase inhibitors include, e.g., oligomycin or 7-Chloro-5-(4-hydroxyphenyl)-1-methyl-3-(napthalen-2-yl-metyl)-4,5-dihydro-1H-benzo[b][1,4]diazepin-2(3H)-one (Bz-423).

Exemplary Protocol

1. Cultured cells are first seeded into the wells of an appropriate microplate (also referred to herein as a multi-well plate) for the instrument being used (as described above).
2. After adherence to the microplate, cells are either allowed to grow as desired, or may be assayed for metabolic potential immediately.
3. At time of assay, cell culture media is exchanged for a volume of assay media appropriate for the microplate being used to create a cell sample including a plurality of cells disposed in a media. The microplate is allowed to incubate for 1 h at 37° C. in a non-$CO_2$ incubator.
4. In some cells, lipopolysaccharide ("LPS") may be added to a final concentration of 1 μg/ml during the change to assay media. The cells may be allowed to incubate for 1 h at 37° C. in a non-$CO_2$ incubator before assay. The LPS treatment may not be removed during the assay.
5. The appropriate instrument is programmed with command instructions to conduct, e.g., three measurements, inject the solution from a port in a cartridge disposed above the cell sample in a well, and then conduct 5 additional measurements.
6. Oligomycin stock solution is prepared to a working concentration of 10 μM in assay media. FCCP is added to this solution to a working concentration optimized for the particular cell type being assayed. For example, in RAW 264.7 macrophages, a working solution of 5 μM is prepared.

Figure 9:
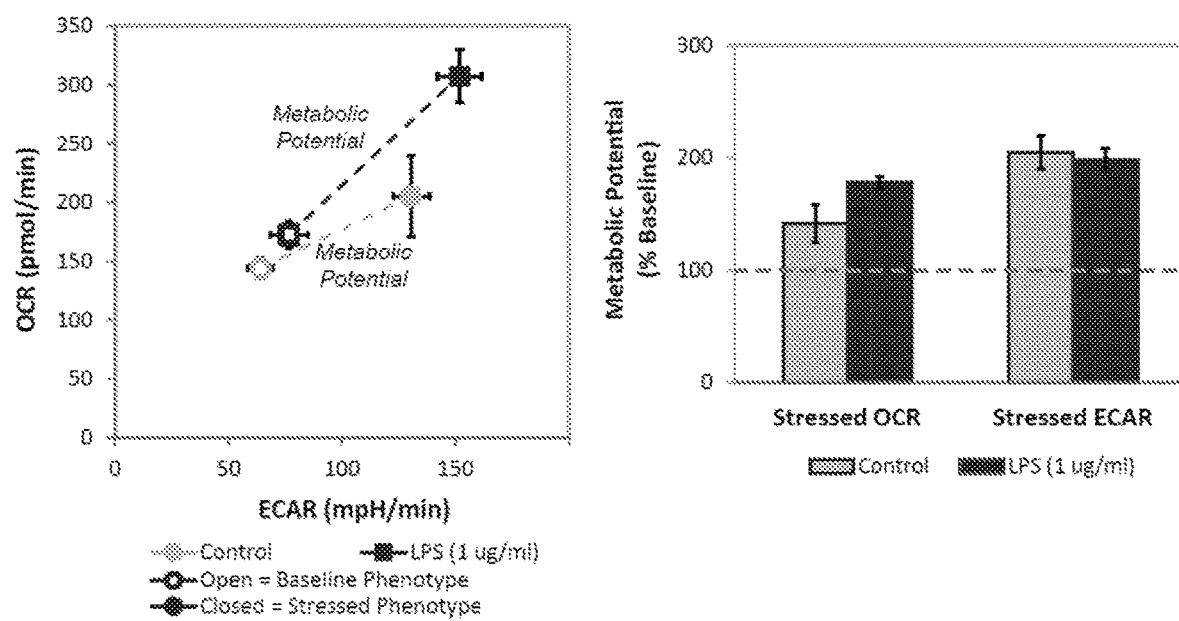
FIG. 9 is a graph of exemplary data that may be generated by certain methods in accordance with embodiments of the invention described herein.
Figure 10:
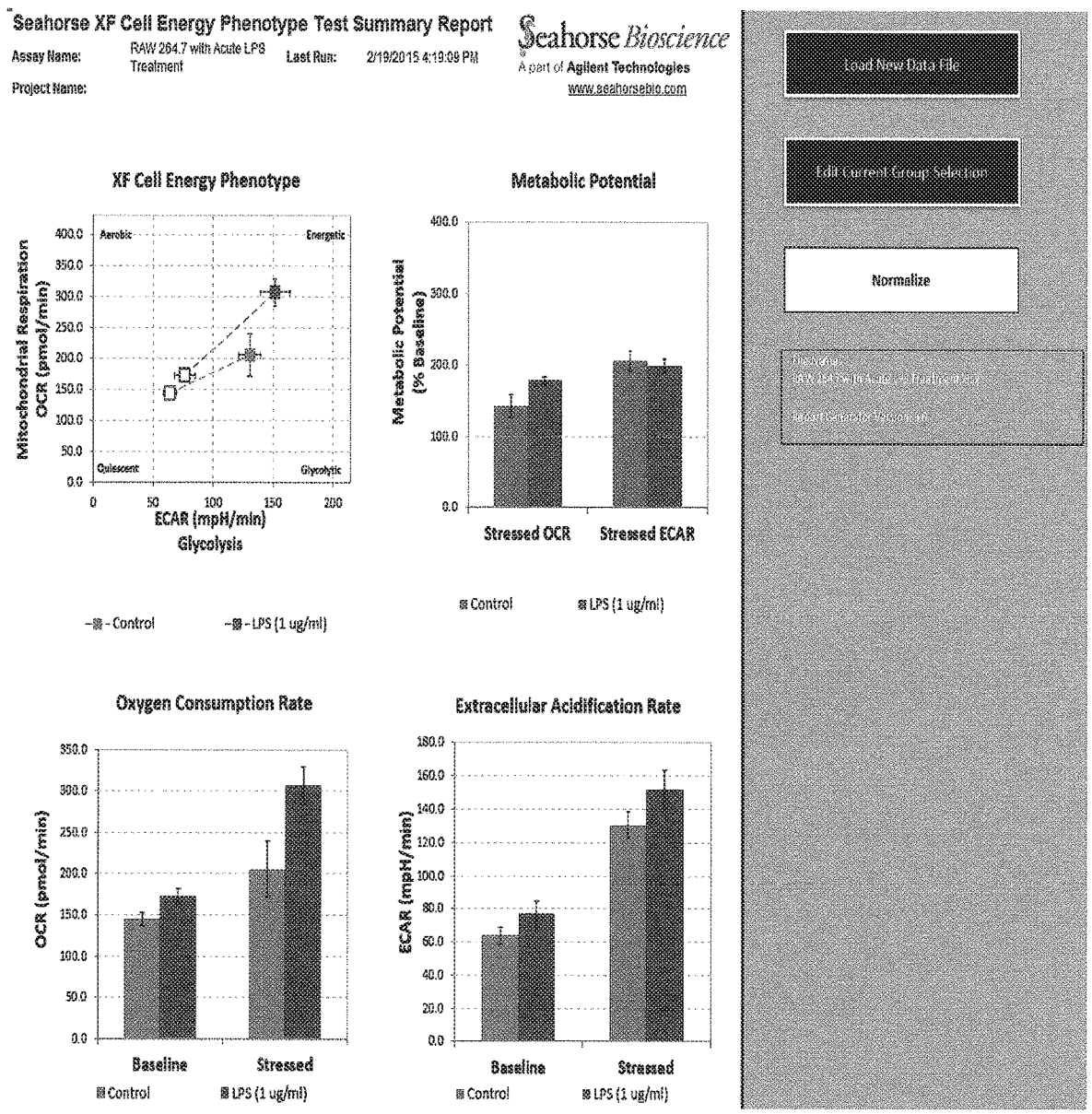
FIG. 10 is a screen shot of an exemplary user interface that may be used in conjunction with certain embodiments of the invention described herein.

7. A sufficient volume of the working solution is added to an assay cartridge such that upon injection the working solution is diluted into the assay medium to the final desired concentration. For example, in RAW 264.7 macrophages, the final desired concentration is 1.0 µM oligomycin and 0.5 µM FCCP. Both of these concentrations were determined by titration for optimal effectiveness.
8. To titrate optimal FCCP concentration in an XFe96 instrument, RAW 264.7 macrophages are exposed to varying concentrations of the drug, and the resulting OCR is measured. In this example, cells were first treated with 1.0 µM oligomycin (final concentration in 200 µl assay media), OCR was measured, and then one of the following concentrations of FCCP was added: 0.125, 0.25, 0.5, 1.0, or 2.0 µM (final concentration in 222 µl assay media). The resulting OCR is then plotted as in the example figure to determine the lowest concentration which achieves maximal stimulation of OCR.
9. The hydrated assay cartridge containing oligomycin and FCCP is loaded into the instrument.
10. After assay cartridge calibration, the cell culture microplate is loaded into the instrument. The instrument then performs the programmed measurement steps as outlined above.
11. The metabolic potential of the cell sample may be determined by (i) providing the initial oxygen consumption rate, the initial extracellular acidification rate, the subsequent oxygen consumption rate, and the subsequent extracellular acidification rate to a software program, and (ii) using the software program to calculate the metabolic potential. Accordingly, at the completion of an experiment, the data may be analyzed using an Excel macro that calculates the metabolic potential based upon the degree of stimulation of each pathway. The Excel macro analyzes the data generated by any XF instrument. Data analysis begins by determining the baseline rate of oxygen consumption and extracellular acidification as defined by the last measurement prior to injection of stressors. The stressed data point is determined using the data point which is stimulated maximally following co-injection of oligomycin and FCCP. These data are plotted graphically where the Y-axis represents OCR and the X axis represents ECAR. Metabolic potential is determined for each element separately by determining the percent stimulation of each pathway (OCR and ECAR) by the stressor above baseline. An example of the types of data that may be generated by certain methods in accordance with embodiments of the invention described herein are presented in FIG. 9. A screen shot of an exemplary user interface that may be used in conjunction with certain embodiments of the invention described herein is presented in FIG. 10.

A suitable assay kit may include tubes of oligomycin and FCCP. The compounds are preferably premeasured, and lyophilized for stability.

Calculations may be performed on the time-resolved data to determine the baseline and stressed phenotypes, as well as the combined metabolic potential. The data may be averaged from multiple technical replicates within a single experimental microplate.

EXAMPLES

Example 1. FCCP Titration in the Presence of Oligomycin in RAW 264.7 Macrophage Cells RAW 264.7 macrophage cells were seeded into XFe96 microplates (Seahorse Bioscience) at a density of $8.0 \times 10^4$ cells/well. Because RAW 264.7 cells are semi-adherent, cells were added to each well and the microplate was then centrifuged at 300×g for two minutes to settle the cells to the bottom of the well. Cells were cultured for 24 hours in DMEM supplemented with 25 mM glucose, 4 mM glutamine, 1 mM pyruvate, and 10% FBS.

Culture media was replaced with assay media (modified DMEM omitting sodium bicarbonate; available from Seahorse Bioscience as XF Base Medium, supplemented with 10 mM glucose, 2 mM glutamine, and 1 mM pyruvate).

FCCP titration was performed using an XFe96 Extracellular Flux Analyzer (Seahorse Bioscience) and XFe96 assay cartridges (Seahorse Bioscience) according to the manufacturer's instructions. Briefly, cells were first treated with 1.0 µM oligomycin (final concentration in 200 µl assay media), OCR was measured, and then one of the following concentrations of FCCP was added: 0.125 µM, 0.25 µM, 0.5 µM, 1.0 µM, or 2 µM (final concentration in 222 µl assay media). The resulting OCR was then plotted as in the example figure to determine the lowest concentration which achieves maximal stimulation of OCR.

Results of the titration are presented in FIG. 1. Data are the oxygen consumption rates of RAW 264.7 macrophage cells in the presence of 1.0 µM oligomycin plus the indicated concentration of FCCP. Data shown are the mean±standard deviation from three replicates per treatment group. These data indicate that maximal OCR is achieved with 0.5 µM FCCP in the presence of 1.0 µM oligomycin.

Example 2. Effects of LPS Treatment on Metabolic Potential in RAW 264.7 Macrophage Cells RAW 264.7 macrophage cells were seeded into XFp microplates at a density of $8.0 \times 10^4$ cells/well. Because RAW 264.7 cells are semi-adherent, cells were added to each well and the microplate was then centrifuged at 300×g for two minutes to settle the cells to the bottom of the well. Cells were cultured for 24 hours in DMEM supplemented with 25 mM glucose, 4 mM glutamine, 1 mM pyruvate, and 10% FBS.

Culture media was replaced with assay media (modified DMEM omitting sodium bicarbonate; available from Seahorse Bioscience as XF Base Medium, supplemented with 10 mM glucose, 2 mM glutamine, and 1 mM pyruvate). Cells treated with LPS received media containing 1 µg/ml LPS, control cells received assay media. Cells were incubated for 1 hour at 37° C. in a non-$CO_2$ incubator before assay.

Metabolic potential was measured using an XFp Extracellular Flux Analyzer (Seahorse Bioscience) and XFp assay cartridges (Seahorse Bioscience). Briefly, microplates containing LPS-treated and control cells were placed in the XFp Extracellular Flux Analyzer, and initial OCR and ECAR measurements are taken. Treated and control wells are then treated simultaneously with 0.5 µM FCCP and 1.0 µM oligomycin (final concentration in 200 µl assay media), and OCR and ECAR measurements were subsequently taken.

Figure 2:
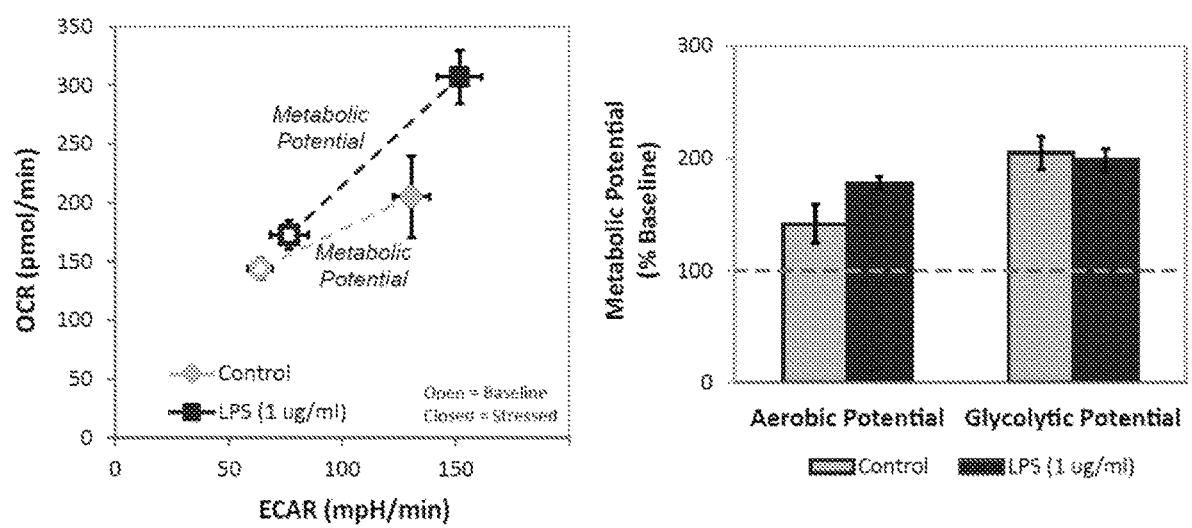
FIG. 2 presents the results from an experiment showing the effects of LPS treatment on Metabolic potential in RAW 264.7 macrophage cells.

Results of the experiment are presented in FIG. 2. Data shown are the mean±standard deviation from three replicates per treatment group. These data indicate that the aerobic metabolic potential of cells treated with LPS is increased relative to control cells, and the glycolytic potential remains roughly unchanged.

Example 3. Effects of Treatment with DCA on Metabolic Potential of Hela Cells

Hela cells were seeded into XFp microplates at a density of $1.2 \times 10^4$ cells/well. Cells were cultured for 24 hours in MEM supplemented with 5.5 mM glucose, 2 mM glutamine, and 10% FBS.

Culture media was replaced with assay media (modified DMEM omitting sodium bicarbonate; available from Seahorse Bioscience as XF Base Medium, supplemented with 10 mM glucose, 2 mM glutamine, and 1 mM pyruvate). Treated cells received media containing 10 mM dichloroacetate (DCA), control cells received assay media. Cells were incubated for 1 hour at 37° C. in a non-$CO_2$ incubator before assay.

Metabolic potential was measured using an XFp Extracellular Flux Analyzer (Seahorse Bioscience) and XFp assay cartridges (Seahorse Bioscience). Briefly, microplates containing DCA-treated and control cells were placed in the XFp Extracellular Flux Analyzer, and initial OCR and ECAR measurements are taken. Treated and control wells are then treated simultaneously with 0.75 µM FCCP and 1.0 µM oligomycin (final concentration in 200 µl assay media), and OCR and ECAR measurements were subsequently taken.

Figure 3:
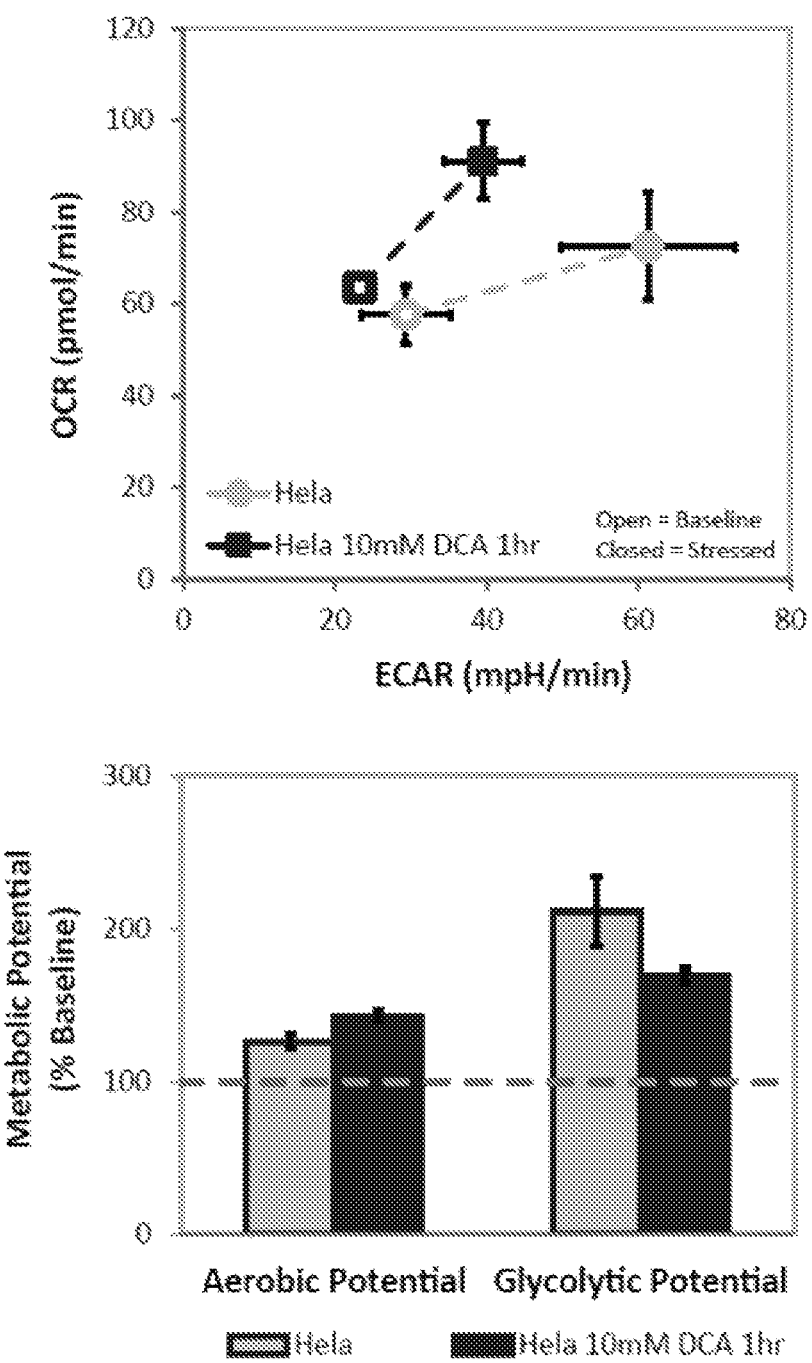
FIG. 3 presents results from an experiment showing the effects of treatment with DCA on metabolic potential of Hela cells.

Results of the experiment are presented in FIG. 3. Data shown are the mean±standard deviation from three replicates per treatment group. These data indicate that the aerobic metabolic potential of treated cells is slightly increased relative to control cells, and the glycolytic potential is decreased.

Example 4. Effects of Treatment with UK5099 on C2C12 Myoblast Cells

C2C12 myoblast cells were seeded into XFp microplates at a density of $1.2 \times 10^4$ cells/well. Cells were cultured for 24 hours in DMEM supplemented with 25 mM glucose, 4 mM glutamine, 1 mM pyruvate, and 10% FBS.

Culture media was replaced with assay media (modified DMEM omitting sodium bicarbonate; available from Seahorse Bioscience as XF Base Medium, supplemented with 10 mM glucose, 2 mM glutamine, and 1 mM pyruvate). Treated cells received media containing 2 µM UK5099 (a potent inhibitor of the mitochondrial pyruvate carrier), control cells received assay media. Cells were incubated for 1 hour at 37° C. in a non-$CO_2$ incubator before assay.

Metabolic potential was measured using an XFp Extracellular Flux Analyzer (Seahorse Bioscience) and XFp assay cartridges (Seahorse Bioscience). Briefly, microplates containing UK5099-treated and control cells were placed in the XFp Extracellular Flux Analyzer, and initial OCR and ECAR measurements are taken. Treated and control wells are then treated simultaneously with 0.5 µM FCCP and 1.0 µM oligomycin (final concentration in 200 µl assay media), and OCR and ECAR measurements were subsequently taken.

Figure 4:
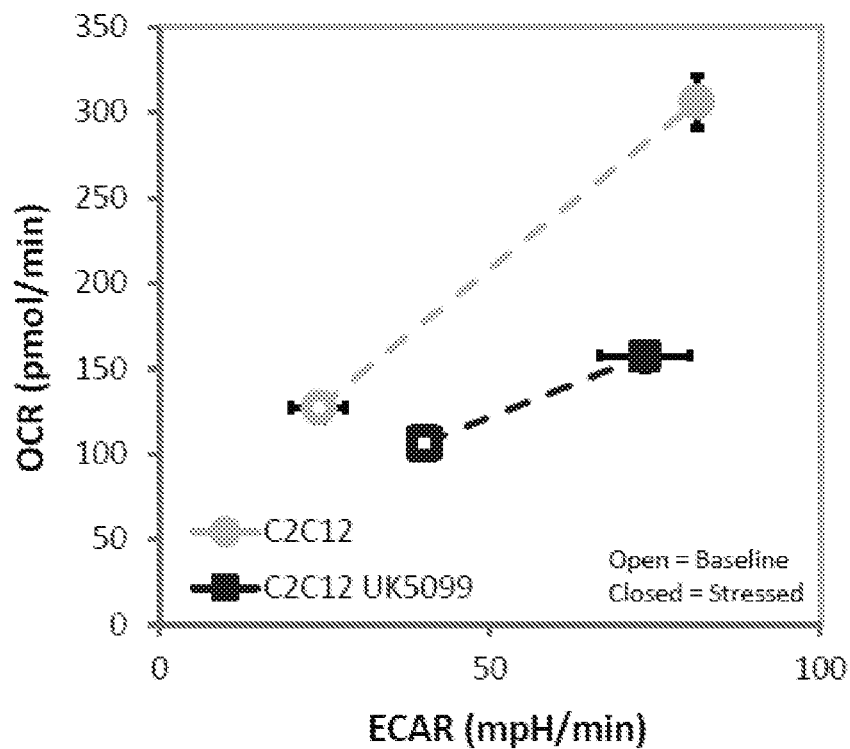
FIG. 4 presents results from an experiment showing the effects of treatment with UK5099 on C2C12 myoblast cells.
Figure 4:
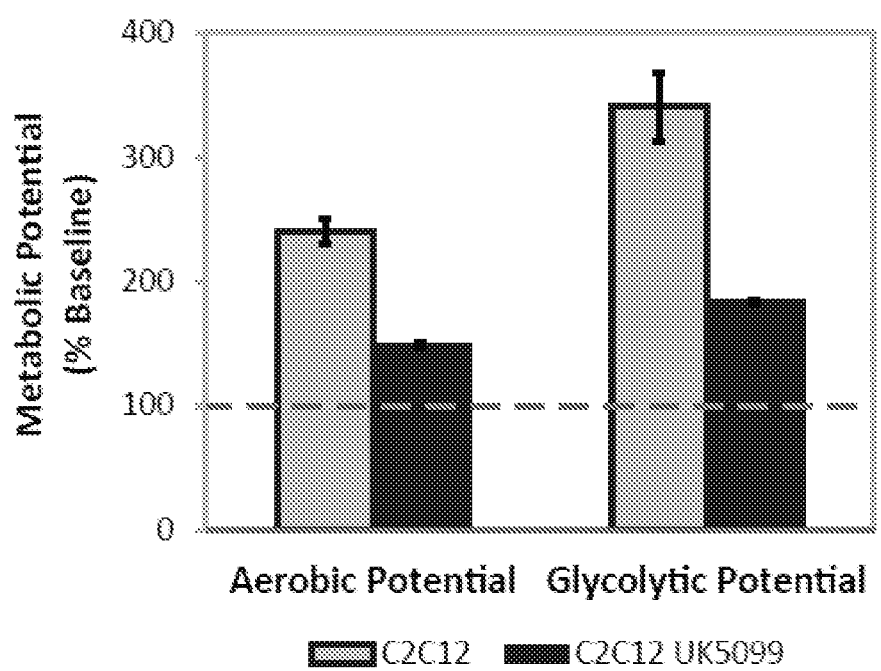

Results of the experiment are presented in FIG. 4. Data shown are the mean±standard deviation from three replicates per treatment group. These data indicate that the aerobic and glycolytic metabolic potential of cells treated with UK5099 is decreased relative to control cells.

Example 5

Example 5 A. Metabolic Potential of A549 Cells

A549 cells were seeded into XFp microplates at a density of $1.0 \times 10^4$ cells/well. Cells were cultured for 24 hours in RPMI 1640 media supplemented with 11 mM glucose, 2 mM glutamine, and 10% FBS.

Culture media was replaced with assay media (modified DMEM omitting sodium bicarbonate; available from Seahorse Bioscience as XF Base Medium, supplemented with 10 mM glucose, 2 mM glutamine, and 1 mM pyruvate). Cells were incubated for 1 hour at 37° C. in a non-$CO_2$ incubator before assay.

Metabolic potential was measured using an XFp Extracellular Flux Analyzer (Seahorse Bioscience) and XFp assay cartridges (Seahorse Bioscience). Briefly, microplates containing cells were placed in the XFp Extracellular Flux Analyzer, and initial OCR and ECAR measurements were taken. Treated and control wells were then treated with 1.0 µM oligomycin (final concentration in 200 µl assay media). After oligomycin treatment, intermediate OCR and ECAR measurements were taken. After 20 minutes, treated and control wells were treated with 0.5 µM FCCP and (final concentration in 200 µl assay media), and final OCR and ECAR measurements were subsequently taken.

Figure 5:
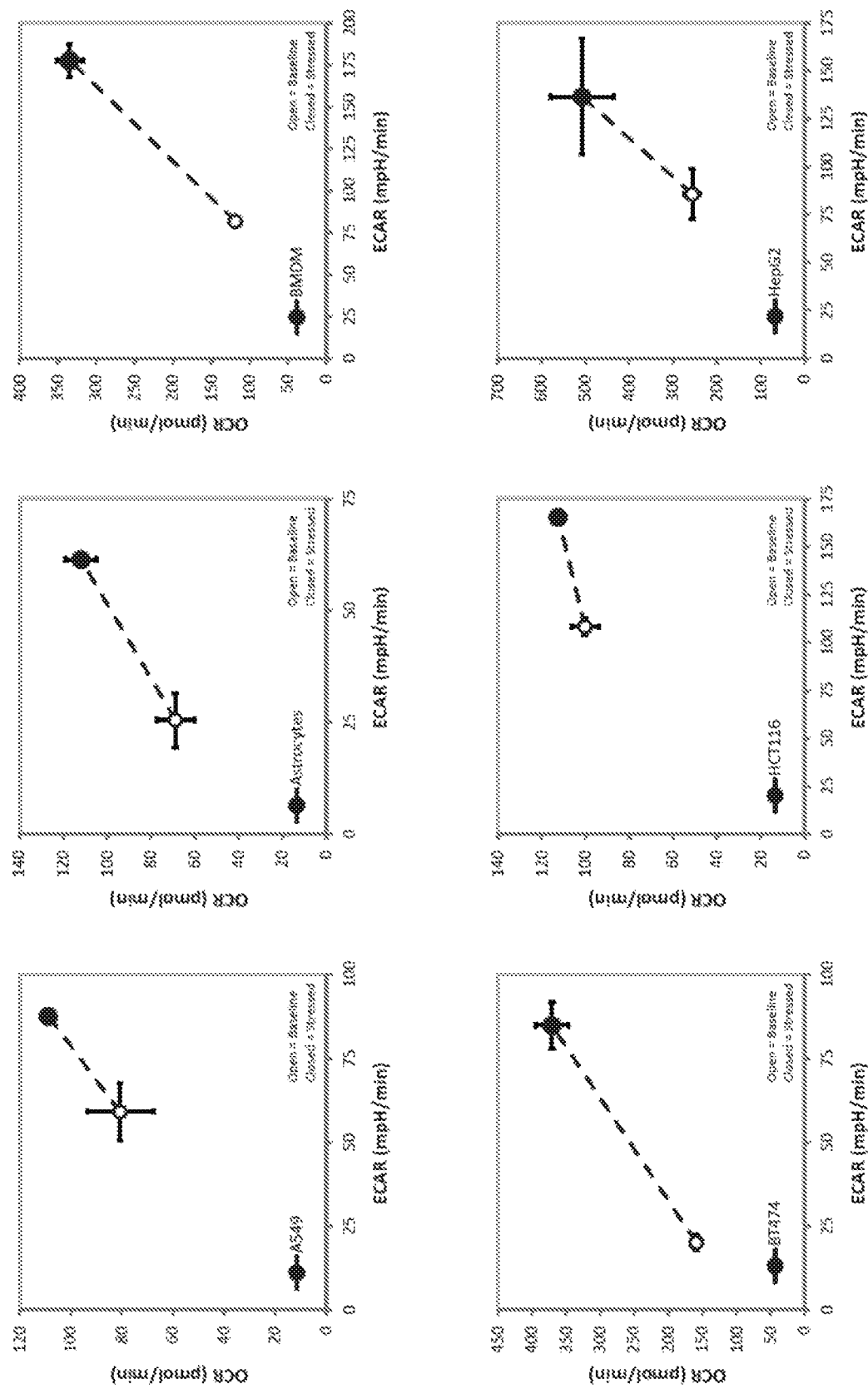
FIG. 5 presents results from experiments showing the metabolic potential of A549 cells, rat astrocytes, primary mouse bone marrow-derived macrophages, BT474 cells, HCT116 cells and HepG2 cells.

Results of the experiment are presented in FIG. 5. Data shown are the mean±standard deviation from three replicates per treatment group.

Example 5 B. Metabolic Potential Rat Astrocytes 14-day post-isolation rat astrocytes were seeded into XFp microplates at a density of $2.0 \times 10^4$ cells/well. Cells were cultured for 48 hours in DMEM supplemented with 5.5 mM glucose, 2 mM glutamine, and 10% FBS.

Culture media was replaced with assay media (modified DMEM omitting sodium bicarbonate; available from Seahorse Bioscience as XF Base Medium, supplemented with 10 mM glucose, 2 mM glutamine, and 1 mM pyruvate). Cells were incubated for 1 hour at 37° C. in a non-$CO_2$ incubator before assay.

Metabolic potential was measured using an XFp Extracellular Flux Analyzer (Seahorse Bioscience) and XFp assay cartridges (Seahorse Bioscience). Briefly, microplates containing cells were placed in the XFp Extracellular Flux Analyzer, and initial OCR and ECAR measurements were taken. Treated and control wells were then treated with 1.0 µM oligomycin (final concentration in 200 µl assay media). After oligomycin treatment, intermediate OCR and ECAR measurements were taken. After 20 minutes, treated and control wells were treated with 2.0 µM FCCP and (final concentration in 200 µl assay media), and final OCR and ECAR measurements were subsequently taken.

Results of the experiment are presented in FIG. 5. Data shown are the mean±standard deviation from three replicates per treatment group.

Example 5 C. Metabolic Potential of Primary Mouse Bone Marrow-Derived Macrophages Primary mouse bone marrow-derived macrophages were differentiated using GM-CSF and grown in culture for 7 days. Cells were seeded into XFp microplates at a density of $8.0 \times 10^4$ cells/well.

Cells were cultured for 24 hours in DMEM supplemented with 10 mM glucose, 2 mM glutamine, 1 mM pyruvate, and 10% FBS.

Culture media was replaced with assay media (modified DMEM omitting sodium bicarbonate; available from Seahorse Bioscience as XF Base Medium, supplemented with 10 mM glucose, 2 mM glutamine, and 1 mM pyruvate). Cells were incubated for 1 hour at 37° C. in a non-$CO_2$ incubator before assay.

Metabolic potential was measured using an XFp Extracellular Flux Analyzer (Seahorse Bioscience) and XFp assay cartridges (Seahorse Bioscience). Briefly, microplates containing cells were placed in the XFp Extracellular Flux Analyzer, and initial OCR and ECAR measurements were taken. Treated and control wells were then treated with 1.0 µM oligomycin (final concentration in 200 µl assay media). After oligomycin treatment, intermediate OCR and ECAR measurements were taken. After 20 minutes, treated and control wells were treated with 1.0 µM FCCP and (final concentration in 200 µl assay media), and final OCR and ECAR measurements were subsequently taken.

Results of the experiment are presented in FIG. 5. Data shown are the mean±standard deviation from three replicates per treatment group.

Example 5 D. Metabolic Potential of BT474 Cells

BT474 cells were seeded into XFp microplates at a density of $2.0 \times 10^4$ cells/well. Cells were cultured for 24 hours in ATCC Hybricare media supplemented with 10% FBS.

Culture media was replaced with assay media (modified DMEM omitting sodium bicarbonate; available from Seahorse Bioscience as XF Base Medium, supplemented with 10 mM glucose, 2 mM glutamine, and 1 mM pyruvate). Cells were incubated for 1 hour at 37° C. in a non-$CO_2$ incubator before assay.

Metabolic potential was measured using an XFp Extracellular Flux Analyzer (Seahorse Bioscience) and XFp assay cartridges (Seahorse Bioscience). Briefly, microplates containing cells were placed in the XFp Extracellular Flux Analyzer, and initial OCR and ECAR measurements were taken. Treated and control wells were then treated with 1.0 µM oligomycin (final concentration in 200 µl assay media). After oligomycin treatment, intermediate OCR and ECAR measurements were taken. After 20 minutes, treated and control wells were treated with 0.5 µM FCCP and (final concentration in 200 µl assay media), and final OCR and ECAR measurements were subsequently taken.

Results of the experiment are presented in FIG. 5. Data shown are the mean±standard deviation from three replicates per treatment group.

Example 5 E. Metabolic Potential of HCT116 Cells

HCT116 cells were seeded into XFp microplates at a density of $1.2 \times 10^4$ cells/well. Cells were cultured for 24 hours in RPMI 1640 media supplemented with 11 mM glucose, 2 mM glutamine, and 10% FBS.

Culture media was replaced with assay media (modified DMEM omitting sodium bicarbonate; available from Seahorse Bioscience as XF Base Medium, supplemented with 10 mM glucose, 2 mM glutamine, and 1 mM pyruvate). Cells were incubated for 1 hour at 37° C. in a non-$CO_2$ incubator before assay.

Metabolic potential was measured using an XFp Extracellular Flux Analyzer (Seahorse Bioscience) and XFp assay cartridges (Seahorse Bioscience). Briefly, microplates containing cells were placed in the XFp Extracellular Flux Analyzer, and initial OCR and ECAR measurements were taken. Treated and control wells were then treated with 1.0 µM oligomycin (final concentration in 200 µl assay media). After oligomycin treatment, intermediate OCR and ECAR measurements were taken. After 20 minutes, treated and control wells were treated with 0.25 µM FCCP and (final concentration in 200 µl assay media), and final OCR and ECAR measurements were subsequently taken.

Results of the experiment are presented in FIG. 5. Data shown are the mean±standard deviation from three replicates per treatment group.

Example 5 F. Metabolic Potential of HepG2 Cells

HepG2 cells were seeded into XFp microplates at a density of $2.0 \times 10^4$ cells/well. Cells were cultured for 24 hours in RPMI 1640 media supplemented with 11 mM glucose, 2 mM glutamine, and 10% FBS.

Culture media was replaced with assay media (modified DMEM omitting sodium bicarbonate; available from Seahorse Bioscience as XF Base Medium, supplemented with 10 mM glucose, 2 mM glutamine, and 1 mM pyruvate). Cells were incubated for 1 hour at 37° C. in a non-$CO_2$ incubator before assay.

Metabolic potential was measured using an XFp Extracellular Flux Analyzer (Seahorse Bioscience) and XFp assay cartridges (Seahorse Bioscience). Briefly, microplates containing cells were placed in the XFp Extracellular Flux Analyzer, and initial OCR and ECAR measurements were taken. Treated and control wells were then treated with 1.0 µM oligomycin (final concentration in 200 µl assay media). After oligomycin treatment, intermediate OCR and ECAR measurements were taken. After 20 minutes, treated and control wells were treated with 0.5 µM FCCP and (final concentration in 200 µl assay media), and final OCR and ECAR measurements were subsequently taken.

Results of the experiment are presented in FIG. 5. Data shown are the mean±standard deviation from three replicates per treatment group.

Example 6

Example 6 A. Metabolic Potential of Human Umbilical Vein Endothelial Cells

Human umbilical vein endothelial cells were seeded into XFp microplates at a density of $1.2 \times 10^4$ cells/well. Cells were cultured for 24 hours in EGM-2 Bulletkit media (Lonza).

Culture media was replaced with assay media (modified DMEM omitting sodium bicarbonate; available from Seahorse Bioscience as XF Base Medium, supplemented with 10 mM glucose, 2 mM glutamine, and 1 mM pyruvate). Cells were incubated for 1 hour at 37° C. in a non-$CO_2$ incubator before assay.

Metabolic potential was measured using an XFp Extracellular Flux Analyzer (Seahorse Bioscience) and XFp assay cartridges (Seahorse Bioscience). Briefly, microplates containing cells were placed in the XFp Extracellular Flux Analyzer, and initial OCR and ECAR measurements were taken. Treated and control wells were then treated with 1.0 µM oligomycin (final concentration in 200 µl assay media). After oligomycin treatment, intermediate OCR and ECAR measurements were taken. After 20 minutes, treated and control wells were treated with 1.0 µM FCCP and (final concentration in 200 µl assay media), and final OCR and ECAR measurements were subsequently taken.

Figure 6:
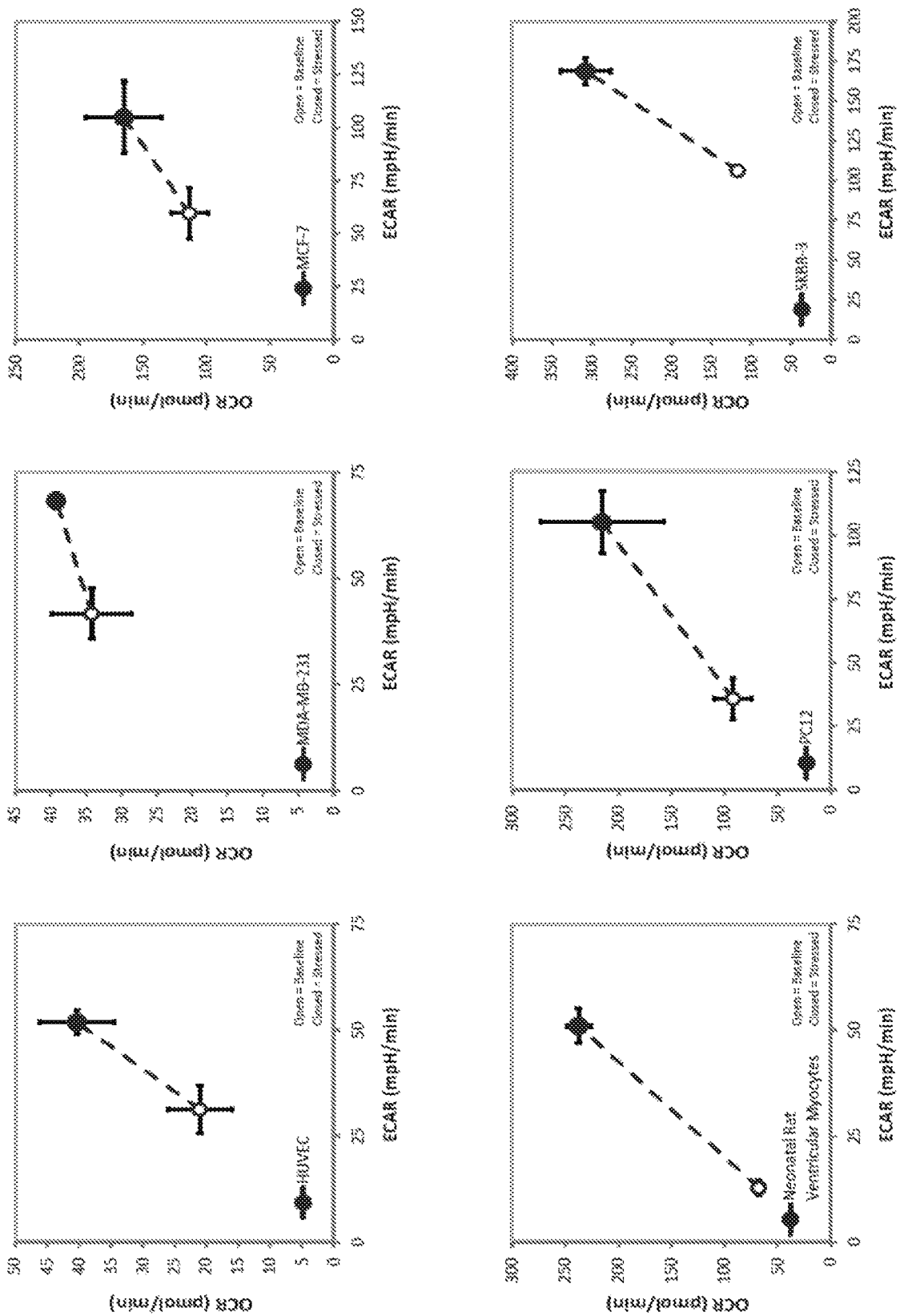
FIG. 6 presents results from experiments showing the metabolic potential of human umbilical vein endothelial cells, MDA-MB-231 cells, MCF-7 cells, neonatal rat ventricular myocytes, PC12 cells and SKBR-3 cells.

Results of the experiment are presented in FIG. 6. Data shown are the mean±standard deviation from three replicates per treatment group.

Example 6 B. Metabolic Potential of MDA-MB-231 Cells

MDA-MB-231 cells were seeded into XFp microplates at a density of $2.0 \times 10^4$ cells/well. Cells were cultured for 24 hours in RPMI 1640 media supplemented with 11 mM glucose, 2 mM glutamine, and 10% FBS.

Culture media was replaced with assay media (modified DMEM omitting sodium bicarbonate; available from Seahorse Bioscience as XF Base Medium, supplemented with 10 mM glucose, 2 mM glutamine, and 1 mM pyruvate). Cells were incubated for 1 hour at 37° C. in a non-$CO_2$ incubator before assay.

Metabolic potential was measured using an XFp Extracellular Flux Analyzer (Seahorse Bioscience) and XFp assay cartridges (Seahorse Bioscience). Briefly, microplates containing cells were placed in the XFp Extracellular Flux Analyzer, and initial OCR and ECAR measurements were taken. Treated and control wells were then treated with 1.0 µM oligomycin (final concentration in 200 µl assay media). After oligomycin treatment, intermediate OCR and ECAR measurements were taken. After 20 minutes, treated and control wells were treated with 1.0 µM FCCP and (final concentration in 200 µl assay media), and final OCR and ECAR measurements were subsequently taken.

Results of the experiment are presented in FIG. 6. Data shown are the mean±standard deviation from three replicates per treatment group.

Example 6 C. Metabolic Potential of MCF-7 Cells

MCF-7 cells were seeded into XFp microplates at a density of $2.0 \times 10^4$ cells/well. Cells were cultured for 24 hours in RPMI 1640 media supplemented with 11 mM glucose, 2 mM glutamine, and 10% FBS.

Culture media was replaced with assay media (modified DMEM omitting sodium bicarbonate; available from Seahorse Bioscience as XF Base Medium, supplemented with 10 mM glucose, 2 mM glutamine, and 1 mM pyruvate). Cells were incubated for 1 hour at 37° C. in a non-$CO_2$ incubator before assay.

Metabolic potential was measured using an XFp Extracellular Flux Analyzer (Seahorse Bioscience) and XFp assay cartridges (Seahorse Bioscience). Briefly, microplates containing cells were placed in the XFp Extracellular Flux Analyzer, and initial OCR and ECAR measurements were taken. Treated and control wells were then treated with 1.0 µM oligomycin (final concentration in 200 µl assay media). After oligomycin treatment, intermediate OCR and ECAR measurements were taken. After 20 minutes, treated and control wells were treated with 0.25 µM FCCP and (final concentration in 200 µl assay media), and final OCR and ECAR measurements were subsequently taken.

Results of the experiment are presented in FIG. 6. Data shown are the mean±standard deviation from three replicates per treatment group.

Example 6 D. Metabolic Potential of Neonatal Rat Ventricular Myocytes

Neonatal rat ventricular myocytes were seeded into XFp microplates at a density of $5.0 \times 10^4$ cells/well. Cells were cultured for 48 hours in DMEM supplemented with 5.5 mM glucose, 2 mM glutamine, and 1 mM pyruvate.

Culture media was replaced with assay media (modified DMEM omitting sodium bicarbonate; available from Seahorse Bioscience as XF Base Medium, supplemented with 10 mM glucose, 2 mM glutamine, and 1 mM pyruvate). Cells were incubated for 1 hour at 37° C. in a non-$CO_2$ incubator before assay.

Metabolic potential was measured using an XFp Extracellular Flux Analyzer (Seahorse Bioscience) and XFp assay cartridges (Seahorse Bioscience). Briefly, microplates containing cells were placed in the XFp Extracellular Flux Analyzer, and initial OCR and ECAR measurements were taken. Treated and control wells were then treated with 1.0 µM oligomycin (final concentration in 200 µl assay media). After oligomycin treatment, intermediate OCR and ECAR measurements were taken. After 20 minutes, treated and control wells were treated with 1.0 µM FCCP and (final concentration in 200 µl assay media), and final OCR and ECAR measurements were subsequently taken.

Results of the experiment are presented in FIG. 6. Data shown are the mean±standard deviation from three replicates per treatment group.

Example 6 E. Metabolic Potential of PC12 Cells

PC12 cells were seeded into XFp microplates at a density of $8.0 \times 10^4$ cells/well. Cells were cultured in assay media (modified DMEM omitting sodium bicarbonate; available from Seahorse Bioscience as XF Base Medium, supplemented with 10 mM glucose, 2 mM glutamine, and 1 mM pyruvate). Cells were incubated for 1 hour at 37° C. in a non-$CO_2$ incubator before assay.

Metabolic potential was measured using an XFp Extracellular Flux Analyzer (Seahorse Bioscience) and XFp assay cartridges (Seahorse Bioscience). Briefly, microplates containing cells were placed in the XFp Extracellular Flux Analyzer, and initial OCR and ECAR measurements were taken. Treated and control wells were then treated with 1.0 µM oligomycin (final concentration in 200 µl assay media). After oligomycin treatment, intermediate OCR and ECAR measurements were taken. After 20 minutes, treated and control wells were treated with 1.0 µM FCCP and (final concentration in 200 µl assay media), and final OCR and ECAR measurements were subsequently taken.

Results of the experiment are presented in FIG. 6. Data shown are the mean±standard deviation from three replicates per treatment group Example 6 F. Metabolic Potential of SKBR-3 Cells SKBR-3 cells were seeded into XFp microplates at a density of $2.0 \times 10^4$ cells/well. Cells were cultured for 24 hours in RPMI 1640 media supplemented with 11 mM glucose, 2 mM glutamine, and 10% FBS.

Culture media was replaced with assay media (modified DMEM omitting sodium bicarbonate; available from Seahorse Bioscience as XF Base Medium, supplemented with 10 mM glucose, 2 mM glutamine, and 1 mM pyruvate). Cells were incubated for 1 hour at 37° C. in a non-$CO_2$ incubator before assay.

Metabolic potential was measured using an XFp Extracellular Flux Analyzer (Seahorse Bioscience) and XFp assay cartridges (Seahorse Bioscience). Briefly, microplates containing cells were placed in the XFp Extracellular Flux Analyzer, and initial OCR and ECAR measurements were taken. Treated and control wells were then treated with 1.0 µM oligomycin (final concentration in 200 µl assay media). After oligomycin treatment, intermediate OCR and ECAR measurements were taken. After 20 minutes, treated and control wells were treated with 1.0 µM FCCP and (final concentration in 200 µl assay media), and final OCR and ECAR measurements were subsequently taken.

Results of the experiment are presented in FIG. 6. Data shown are the mean±standard deviation from three replicates per treatment group.

Example 7. Effects of Etomoxir on the Metabolic Potential of C2C12 Myotubes

C2C12 myoblast cells were seeded into XFp microplates at a density of $1.2 \times 10^4$ cells/well. Cells were cultured for 24 hours in DMEM supplemented with 25 mM glucose, 4 mM glutamine, 1 mM pyruvate, and 10% FBS. This media was then removed and replaced with differentiation media comprised of DMEM supplemented with 25 mM glucose, 4 mM glutamine, 1 mM pyruvate, and 2% horse serum, and allowed to differentiate into myotubes for 4 days. During differentiation, medium was replaced with fresh differentiation medium every other day.

Culture media was replaced with assay media (modified DMEM omitting sodium bicarbonate; available from Seahorse Bioscience as XF Base Medium, supplemented with 10 mM glucose, 2 mM glutamine, and 1 mM pyruvate). Treated myotubes received media containing 40 µM etomoxir (an inhibitor of carnitine-palmitoyl transferase-1, which is involved in fatty acid oxidation), control myotubes received assay media. myotubes were incubated for 1 hour at 37° C. in a non-$CO_2$ incubator before assay.

Metabolic potential was measured using an XFp Extracellular Flux Analyzer (Seahorse Bioscience) and XFp assay cartridges (Seahorse Bioscience). Briefly, microplates containing etomoxir-treated and control myotubes were placed in the XFp Extracellular Flux Analyzer, and initial OCR and ECAR measurements are taken. Treated and control wells are then treated simultaneously with 0.5 µM FCCP and 1.0 µM oligomycin (final concentration in 200 µl assay media), and OCR and ECAR measurements were subsequently taken.

Figure 7:
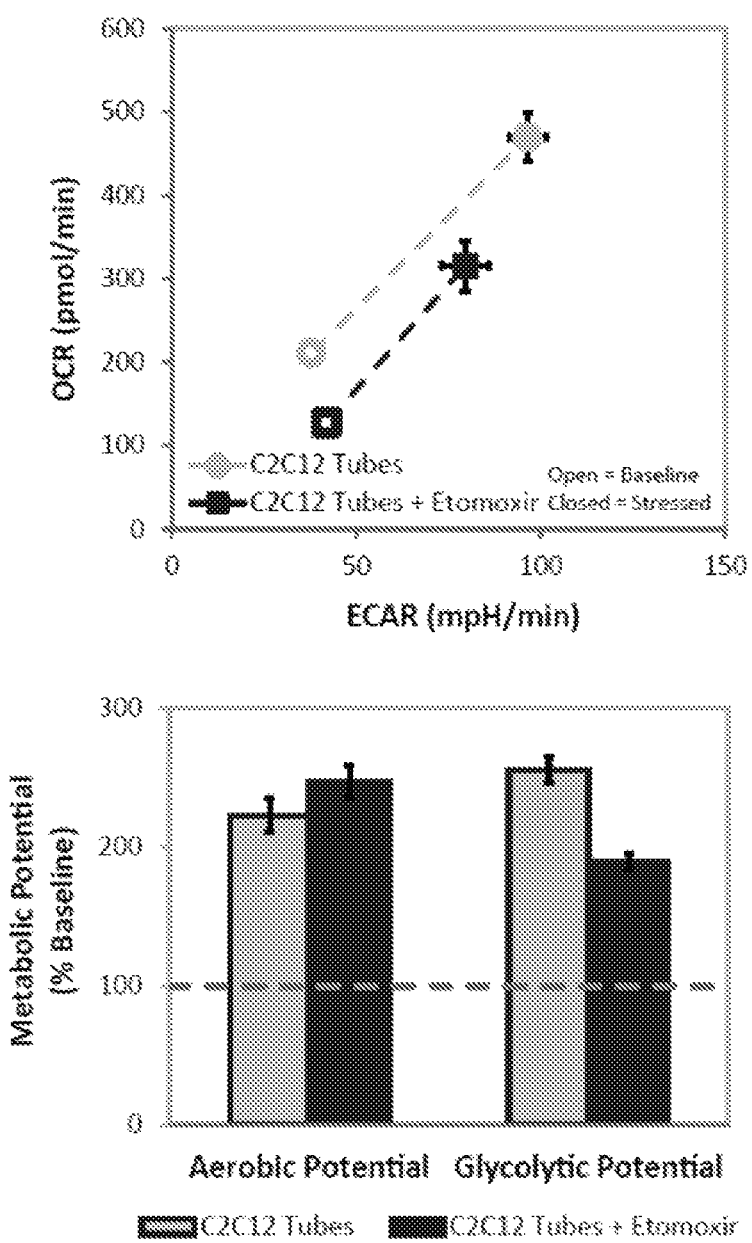
FIG. 7 presents results from an experiment showing the effects of etomoxir on the metabolic potential of C2C12 myotubes.

Results of the experiment are presented in FIG. 7. Data shown are the mean±standard deviation from three replicates per treatment group. These data indicate that the aerobic metabolic potential was increased and glycolytic metabolic potential was slightly decreased in myotubes treated with etomoxir compared to control myotubes.

Example 8. Effects of Treatment with Rapamycin on Metabolic Potential of Jurkat Cells Jurkat cells were seeded into XFp microplates at a density of $1.0 \times 10^5$ cells/well. Because Jurkat cells are semi-adherent, cells were added to each well and the microplate was then centrifuged at 300×g for two minutes to settle the cells to the bottom of the well. Cells were cultured for 24 hours in RPMI 1640 supplemented with Geneticin, 11 mM glucose, 2 mM glutamine, and 10% FBS. Cells in the treatment group were cultured for 24 hours in media containing 10 nM rapamycin (an inhibitor of mTORC1).

Culture media was replaced with assay media (modified DMEM omitting sodium bicarbonate; available from Seahorse Bioscience as XF Base Medium, supplemented with 10 mM glucose, 2 mM glutamine, and 1 mM pyruvate). Cells were incubated for 1 hour at 37° C. in a non-$CO_2$ incubator before assay.

Metabolic potential was measured using an XFp Extracellular Flux Analyzer (Seahorse Bioscience) and XFp assay cartridges (Seahorse Bioscience). Briefly, microplates containing DCA-treated and control cells were placed in the XFp Extracellular Flux Analyzer, and initial OCR and ECAR measurements are taken. Treated and control wells are then treated simultaneously with 0.5 µM FCCP and 1.0 µM oligomycin (final concentration in 200 µl assay media), and OCR and ECAR measurements were subsequently taken.

Figure 8:
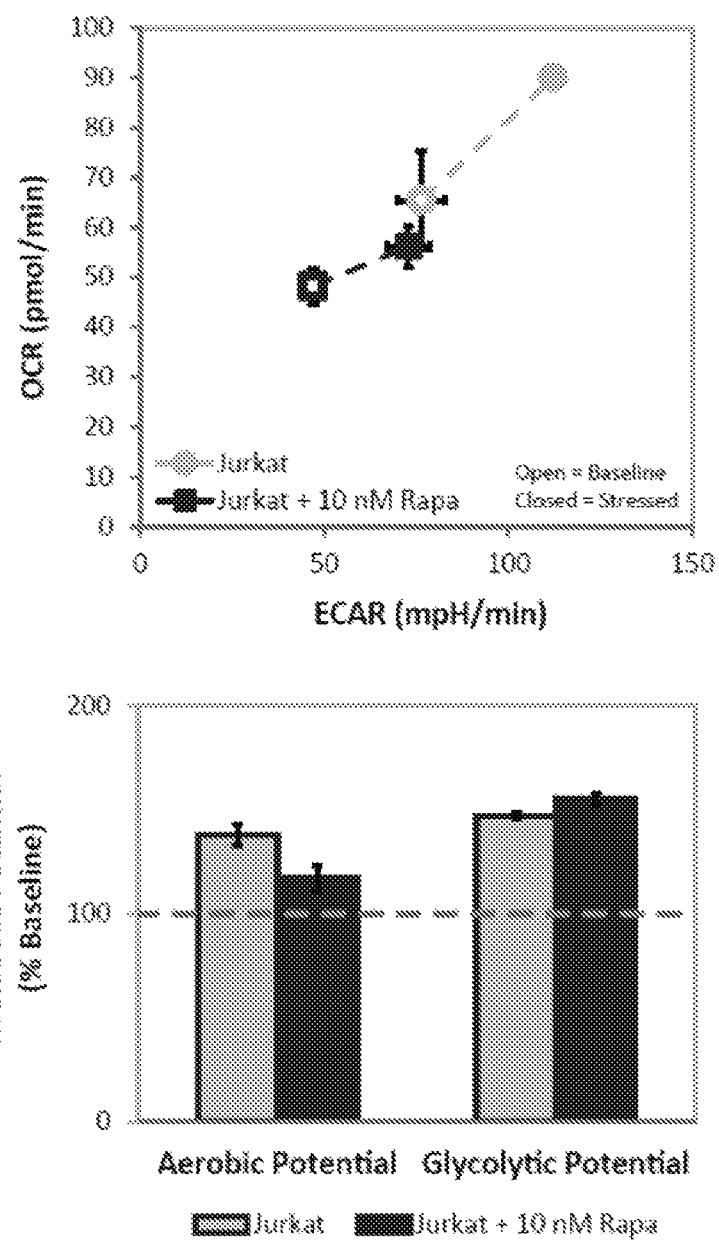
FIG. 8 presents results from an experiment showing the effects of treatment with rapamycin on metabolic potential of Jurkat cells.

Results of the experiment are presented in FIG. 8. Data shown are the mean±standard deviation from three replicates per treatment group. These data indicate that treatment with rapamycin decreased the basal and stressed OCR and ECAR levels in Jurkat cells, and decreased aerobic metabolic potential, but slightly increased glycolytic potential relative to controls.

While several aspects of the present invention have been described and depicted herein, alternative aspects may be effected by those skilled in the art to accomplish the same objectives. Accordingly, it is intended that the appended claims cover all such alternative aspects as fall within the true spirit and scope of the invention.

What is claimed is:

1. A method of determining a single metabolic potential of a cell sample that is representative of both mitochondrial respiration and glycolysis, the method comprising the steps of:
    measuring an initial oxygen consumption rate and an initial extracellular acidification rate of the cell sample;
    thereafter, simultaneously administering to the cell sample a mitochondrial uncoupling agent and an ATP synthase inhibitor;
    thereafter, simultaneously measuring a subsequent oxygen consumption rate and a subsequent extracellular acidification rate of the cell sample; and
    determining a single metabolic potential of the cell sample that is representative of both mitochondrial respiration and glycolysis, wherein the single metabolic potential is plotted graphically where the Y axis represents oxygen consumption rate and the X axis represents extracellular acidification rate.

2. The method of claim 1, wherein at least one of the mitochondrial uncoupling agents comprises carbonyl cyanide p-trifluoromethoxyphenylhydrazone ("FCCP"), carbonyl cyanide-m-chlorophenylhydrazone ("CCCP") or 2,4-dinitrophenol ("DNP") or BAM15, and the ATP synthase inhibitor comprises oligomycin or 7-Chloro-5-(4-hydroxyphenyl)-1-methyl-3-(napthalen-2-ylmetyl)-4,5,-dihydro-1H-benzo[b][1,4]diazepin-2(3H)-one (Bz-423).

3. The method of claim 2, wherein the mitochondrial uncoupling agent comprises carbonyl cyanide p-trifluoromethoxyphenylhydrazone ("FCCP") and the ATP synthase inhibitor comprises oligomycin.

4. The method of claim 1, wherein the cell sample comprises a plurality of cells disposed in a media.

5. The method of claim 4, wherein measuring the initial oxygen consumption rate comprises sensing a cell constituent disposed in the media.

6. The method of claim 4, wherein measuring the initial extracellular acidification rate of the cell sample comprises sensing a cell constituent disposed in the media.

7. The method of claim 4, wherein a concentration of the administered mitochondrial uncoupling agent in the media is in a range of about 0.1 µM to about 2.0 µM.

8. The method of claim 7, wherein the concentration of the administered mitochondrial uncoupling agent in the media is about 0.5 µM.

9. The method of claim 4, wherein a concentration of the administered ATP synthase inhibitor in the media is about 0.1 µM to about 2 µM.

10. The method of claim 9, wherein the concentration of the administered ATP synthase inhibitor in the media is about 1.0 µM.

11. The method of claim 1, further comprising the step of mixing the mitochondrial uncoupling agent and the ATP synthase inhibitor prior to administering to the cell sample.

12. The method of claim 1, further comprising the step of disposing the cell sample in a well of a multi-well plate prior to simultaneously measuring the initial oxygen consumption rate and the initial extracellular acidification rate of the cell sample.

13. The method of claim 12, wherein administering the mitochondrial uncoupling agent and the ATP synthase inhibitor comprises introducing the agent and the inhibitor simultaneously into the well from at least one port.

14. The method of claim 1, wherein determining the metabolic potential of the cell sample comprises (i) providing the initial oxygen consumption rate, the initial extracellular acidification rate, the subsequent oxygen consumption rate, and the subsequent extracellular acidification rate to a software program, and (ii) using the software program to calculate the metabolic potential.

15. The method of claim 1, wherein the initial oxygen consumption rate and an initial extracellular acidification rate of the cell sample are measured simultaneously.

* * * * *